(12) United States Patent
Butler et al.

(10) Patent No.: US 8,486,148 B2
(45) Date of Patent: Jul. 16, 2013

(54) HINGED SPINAL FUSION CAGES

(75) Inventors: Michael S. Butler, St. Charles, IL (US);
Brian D. Hartsell, Aurora, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 390 days.

(21) Appl. No.: 12/355,557

(22) Filed: Jan. 16, 2009

(65) Prior Publication Data
US 2009/0182431 A1 Jul. 16, 2009

Related U.S. Application Data

(60) Provisional application No. 61/011,293, filed on Jan. 16, 2008.

(51) Int. Cl.
*A61F 2/44* (2006.01)
(52) U.S. Cl.
USPC ........................................................ 623/17.16
(58) Field of Classification Search
USPC .................... 623/17.11–17.16; 606/247–249
See application file for complete search history.

(56) References Cited

U.S. PATENT DOCUMENTS

| | | | | |
|---|---|---|---|---|
| 5,171,278 A * | 12/1992 | Pisharodi | ...................... | 128/898 |
| 5,258,031 A * | 11/1993 | Salib et al. | .................. | 623/17.15 |
| 5,425,773 A * | 6/1995 | Boyd et al. | ................... | 623/17.15 |
| 5,554,191 A * | 9/1996 | Lahille et al. | ................ | 623/17.11 |
| 5,562,738 A * | 10/1996 | Boyd et al. | ................... | 623/17.15 |
| 5,653,763 A * | 8/1997 | Errico et al. | ................. | 623/17.11 |
| 6,039,761 A * | 3/2000 | Li et al. | ........................ | 623/17.16 |
| 6,102,950 A * | 8/2000 | Vaccaro | ....................... | 623/17.16 |
| 6,126,689 A * | 10/2000 | Brett | ............................ | 623/17.16 |
| 6,193,757 B1 * | 2/2001 | Foley et al. | ................. | 623/17.16 |
| 6,206,923 B1 * | 3/2001 | Boyd et al. | .................. | 623/17.11 |
| 6,342,055 B1 * | 1/2002 | Eisermann et al. | ........ | 623/17.16 |
| 6,395,031 B1 * | 5/2002 | Foley et al. | ................. | 623/17.11 |
| 6,685,742 B1 * | 2/2004 | Jackson | ...................... | 623/17.11 |
| 2002/0052656 A1 * | 5/2002 | Michelson | ................. | 623/17.11 |
| 2002/0072801 A1 * | 6/2002 | Michelson | ................. | 623/17.11 |
| 2002/0077702 A1 * | 6/2002 | Castro | ........................ | 623/17.16 |
| 2004/0181282 A1 * | 9/2004 | Zucherman et al. | ....... | 623/17.11 |
| 2004/0254643 A1 | 12/2004 | Jackson | | |
| 2005/0119747 A1 * | 6/2005 | Fabris Monterumici et al. | ......................... | 623/17.11 |
| 2006/0030943 A1 * | 2/2006 | Peterman | ................... | 623/17.11 |
| 2006/0142858 A1 * | 6/2006 | Colleran et al. | .......... | 623/17.11 |
| 2007/0260314 A1 | 11/2007 | Biyani | | |

(Continued)

*Primary Examiner* — Mary Hoffman
(74) *Attorney, Agent, or Firm* — Foley & Lardner LLP (57) ABSTRACT

A spinal interbody fusion cage has a body whose anterior/posterior profile may be varied through angular positioning of one or more articulating segments of the body without changing the superior/inferior height of the body. The present spinal interbody fusion cage has N segments or sections wherein at least one segment is articulated relative to another segment via a connection point, pivot or pivot structure such that the anterior/posterior profile is variable through angular positioning of one or more of the segments. The pivot structure may be configured so as to allow unidirectional movement between the connecting segments thereby allowing articulation in one plane or to allow omni-directional movement between the connecting segments thereby allowing articulation in multiple planes. The various forms of the present interbody fusion cage include superior and inferior sides or bone abutment surfaces that have serrations, teeth or similar functioning structures (teeth). The teeth extend between the anterior end and the posterior end. The teeth may take different shapes but are configured to allow insertion of the spinal interbody fusion cage in an anterior-first manner while preventing and/or inhibiting the spinal interbody fusion cage from backing out posteriorly.

22 Claims, 8 Drawing Sheets

U.S. PATENT DOCUMENTS

2008/0125865 A1* 5/2008 Abdelgany ................ 623/17.16
2009/0048676 A1* 2/2009 Fabian, Jr. ................ 623/17.16
2009/0093847 A1* 4/2009 Wilcox ........................ 606/259
2009/0143859 A1* 6/2009 McClellan, III et al. .. 623/17.16

* cited by examiner

HINGED SPINAL FUSION CAGES

RELATED APPLICATIONS

This patent application claims the benefit of and/or priority to U.S. Provisional Patent Application Ser. No. 61/011,293 filed Jan. 16, 2008, entitled "Spinal Interbody Fusion Cages Providing Variable Anterior/Posterior Profiles" the entire contents of which is specifically incorporated herein by this reference.

BACKGROUND OF THE INVENTION

1. Field of the Invention

The present invention relates to spinal interbody devices for implantation between a pair of adjacent vertebrae in order to provide distraction and support to the adjacent vertebrae and/or promote bone fusion between the adjacent vertebrae.

2. Background Information

The disc between vertebrae of a human spine is sometimes damaged due to disease or injury, or may simply deteriorate due to age, disease, injury or congenital defect. With others, the vertebrae may become compressed or otherwise damaged. In these and other cases the vertebrae can become too closely spaced anteriorly which causes an undesired abnormal curvature of the spine with respect to lordosis or kyphosis.

Because of this, surgery may be utilized to place one or more devices between adjacent vertebrae in order to provide proper spacing of the adjacent vertebrae. Such devices may also be used to promote fusion between the vertebrae. When a device of this type is utilized for the purpose of promoting fusion, it is often termed an intervertebral or interbody fusion cage. When so utilized, bone or bone fusion material is often placed about or in the interbody cage in order to promote growth of the bone between the adjacent vertebrae.

One or more interbody fusion cages may be used. When multiple interbody fusion cages are used, bone fusion material may be packed between the interbody fusion cages that are then placed close to one another to promote bone growth and thus fusion.

It is desirable for the interbody fusion cage to engage as much surface of the bone as possible in order to provide proper support to the bone and thereby reduce the likelihood of subsidence of the device into the bone resulting from contact pressure of the interbody fusion cage against bone surfaces. Subsidence can occur since part of the bone is somewhat spongy in nature, especially near the center of the vertebra. In summation, the structure of interbody devices functions to support the two adjacent vertebral surfaces and to promote fusion of the adjacent vertebrae when packed with bone fusion material.

Current intervertebral devices are essentially static in configuration. An exception to this is with regard to height of the intervertebral device wherein it is known to have height adjustable intervertebral devices. However, because factors such as vertebral damage and/or individual anatomy can limit or dictate what type, size and or configuration of intervertebral device can be used with respect to the contact area or placement of the intervertebral device relative to adjacent vertebrae, it would be desirable to have an intervertebral device whose shape can be varied to accommodate such unpredictability.

SUMMARY OF THE INVENTION

The present invention is a spinal interbody fusion cage defining a body whose anterior/posterior profile may be varied through angular positioning of one or more articulated segments of the body. The present spinal interbody fusion cage is formed of a biocompatible material such as PEEK (polyetheretherketone), another polymer or plastic, titanium, stainless steel, a metal alloy, composite or the like.

In one form, the present spinal interbody fusion cage has N segments or sections wherein at least one segment is articulated relative to another segment via a connection point or pivot. The anterior/posterior profile is variable through angular positioning of one or more of the segments. Through controlled angulation of the articulating segments of the body, the anterior/posterior and lateral profile of the spinal interbody fusion cage may be changed as necessary without changing the superior/inferior height of the body.

Articulation between segments is achieved via a pivot structure between the two segments. The pivot structure may be configured so as to allow unidirectional movement between the connecting segments (i.e. allow articulation in one plane, such as via an "S" type hinge) or omni-directional movement between the connecting segments (i.e. allow articulation in multiple planes, such as a ball joint or "U" type hinge). The pivot structure may incorporate a PEEK snap or other PEEK attachment structure.

In another form, the spinal interbody fusion cage may be defined by a body having a first segment and a second segment that is pivotally attached to the first segment such that the second segment is movable in a lateral direction relative to the first segment. Pivotal attachment is achieved through mutually cooperating portions of the connecting segments.

The amount of lateral angulation between any two segments relative to an axis therebetween (a null position) is determined by anterior surface characteristics and/or configuration of one segment and the posterior surface characteristics and/or configuration of the second segment. One or both of the anterior and posterior surfaces of the first and second segments are angled to provide an upward limit of angulation defined by the angle and/or distance between the anterior and posterior surfaces.

The various forms of the present interbody fusion cage include superior and inferior sides or bone abutment surfaces that have serrations, teeth or similar functioning structures (teeth). The teeth extend between the anterior end and the posterior end. The teeth may take different shapes but are configured to allow insertion of the spinal interbody fusion cage in an anterior-first manner while preventing and/or inhibiting the spinal interbody fusion cage from backing out posteriorly.

In their various forms, the bodies, segments, portions or sections of the present interbody spinal fusion cage includes one or more cavities preferably, but not necessarily for the reception of bone fusion material. In one form, a first segment defines a first interior cavity for receipt of bone fusion material while the second segment likewise includes a second interior cavity for receipt of bone fusion material. The first and second cavities are configured to preferably, but not necessarily across the length thereof, extend from the superior to inferior sides of the respective first and second segment.

BRIEF DESCRIPTION OF THE DRAWINGS

The above mentioned and other features, advantages and objects of this invention, and the manner of attaining them, will become apparent and the invention itself will be better understood by reference to the following description of embodiments of the invention taken in conjunction with the accompanying drawings, wherein.

Like reference numerals indicate the same or similar parts throughout the several figures.

A discussion of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF EMBODIMENTS OF THE INVENTION

Referring to FIGS. 1-5, there is depicted an exemplary embodiment of a spinal interbody fusion cage or device, generally designated 10, fashioned in accordance with the present principles such that its 1) anterior to posterior (or posterior to anterior) profile and 2) lateral profile is changeable while its inferior to superior (or superior to inferior) height or profile remains constant. This is accomplished through angular positioning of a laterally pivoting portion of the body as described herein. The spinal interbody fusion cage 10 is utilized for implantation between a pair of adjacent vertebrae in order to provide distraction and support to the adjacent vertebrae and/or promote bone fusion between the adjacent vertebrae. The spinal interbody fusion cage 10 is sized to be received between the adjacent vertebrae and not extend beyond the periphery of the vertebrae. As such, the fusion cage 10 may be fabricated in various sizes to accommodate various sizes of lumbar vertebrae. In a preferred form, the spinal interbody fusion cage 10 is formed of a biocompatible PEEK (polyetheretherketone) but may be formed of another biocompatible material such as titanium, a titanium alloy, stainless steel, a polymer, plastic, composite or the like.

The spinal interbody fusion cage or body 10 is defined by a generally rectangular first body portion or segment 12 to which is pivotally coupled a generally rectangular second body portion or segment 14. It should be appreciated that the first and second body portions 12 and 14 may take other shapes as desired. The first body portion 12 has a superior side 13 and an inferior side (not seen in the figures and thus not labeled) that is opposite to the superior side 13. The first body portion 12 also defines a posterior side or surface 16 and an opposite anterior side (not labeled). The posterior side 16 is generally flat with a bore 17 therein that allows the use of a tool (not shown) to insert the fusion cage 10 into a disc space. Transitions between the various sides are a product of the teeth cuts or configuration. The inferior side of the first body portion 12 has an arcuate portion 38 therein that defines a pivot seat. The first body portion 12 further defines opposite lateral sides or surfaces 20 and 22 that each extends between the superior and inferior sides thereof. The lateral sides 20, 22 are generally, but not necessarily flat.

The superior side 13 of the first body portion 12 has a gripping surface that is characterized by a plurality of serrations, teeth or teeth structures 42 that define plateaus and valleys for contact with an upper vertebral body (vertebra). The plurality of teeth 42 are configured to allow insertion of the first body portion 12 (and thus the fusion cage 10) via the anterior, posterior, or lateral side of the spine but prevent the backing out therefrom. In this regard, the teeth 42 are oriented accordingly (see e.g. FIGS. 1 and 3). Likewise, the inferior side of the first body portion 12 has a gripping surface that is characterized by a plurality of serrations, teeth or teeth structures 44 that define plateaus and valleys for contact with a lower vertebral body (vertebra). The plurality of teeth 44 are likewise configured to allow insertion of the first body portion 12 (and thus the fusion cage 10) via the anterior, posterior, or lateral side of the spine but prevent the backing out therefrom. In this regard, the teeth 44 are oriented accordingly.

Figure 1:
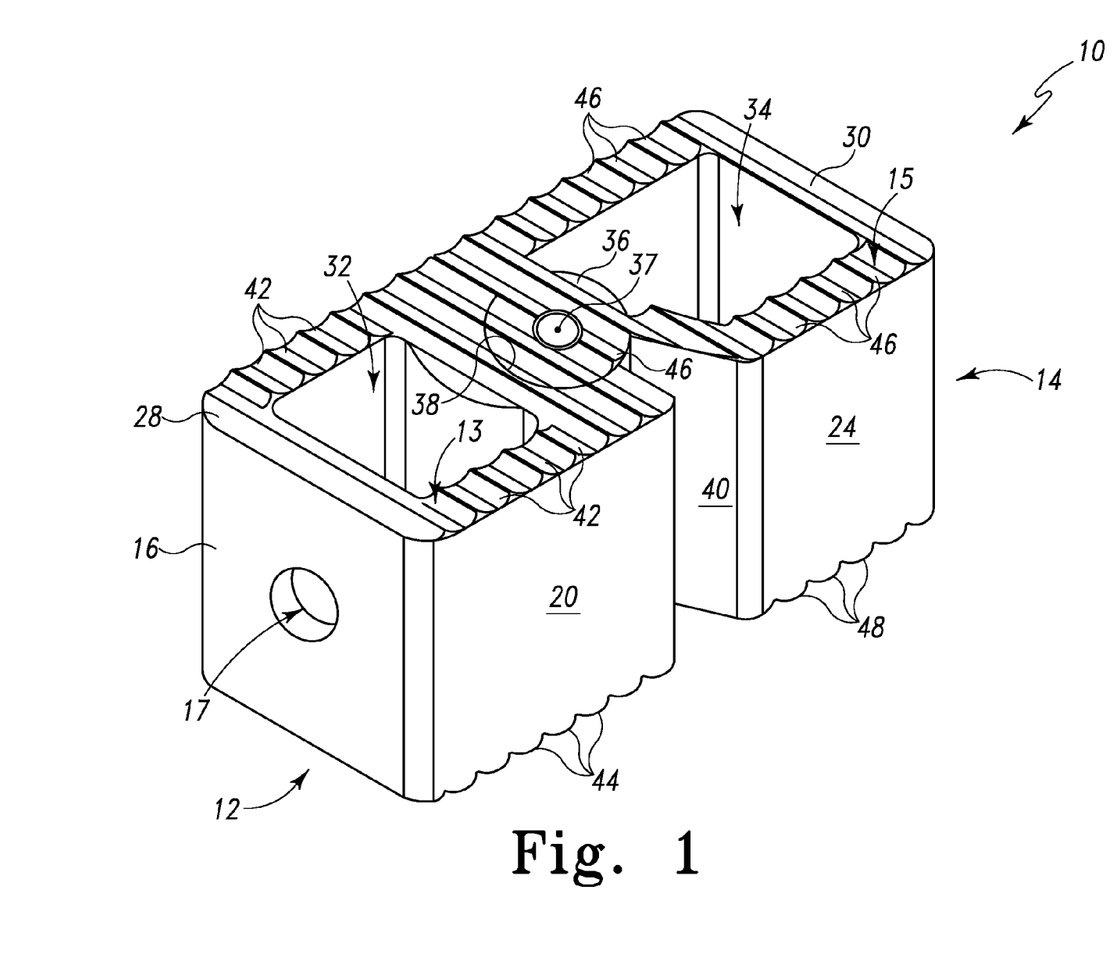
FIG. 1 is a posterior perspective view of an exemplary embodiment of a spinal interbody fusion cage having a variable anterior/posterior profile fashioned in accordance with the present principles, the spinal interbody fusion cage shown with a pivoting portion thereof in a null or non-angled anterior/posterior position.
Figure 3:
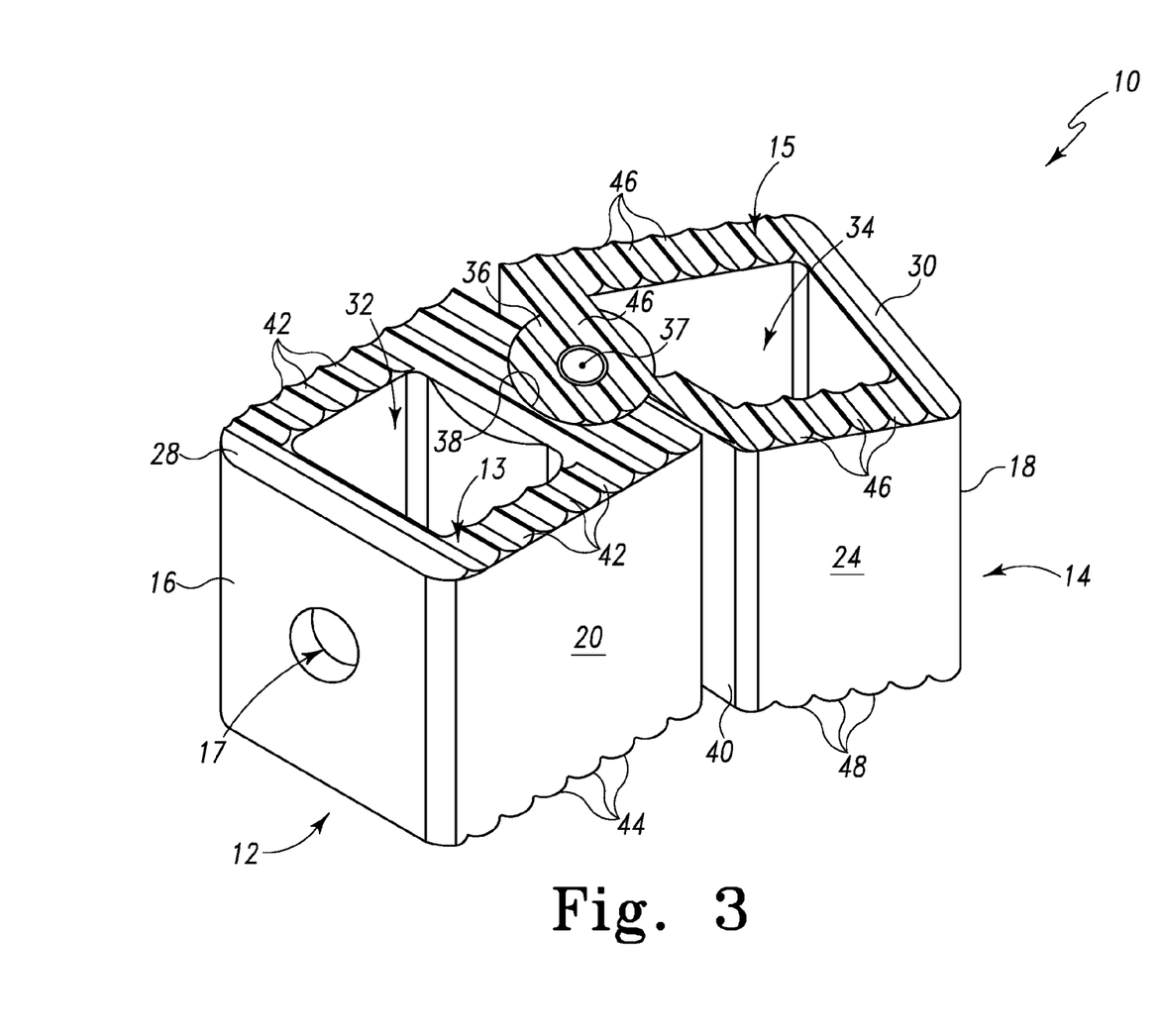
FIG. 3 is a posterior perspective view of the spinal interbody fusion cage of FIG. 1 with the pivoting portion thereof in a full angled position.

The first body portion 12 moreover includes a first cavity 32 that extends between the superior side 13 and the inferior side (not labeled) of the first body portion 12. Bone fusion material is received in the first cavity 32 to promote vertebral fusion. As such, the first cavity 32 is open at the superior side and the inferior side of the first body portion 12.

The second body portion 14 has a superior side 15 and an inferior side (not seen in the figures and thus not labeled) that is opposite to the superior side 15. The second body portion 14 also defines a generally flat anterior side or surface 18 and an opposite posterior side (not labeled). The anterior surface 18 transitions to the superior surface 15 via a tapered surface 30 and likewise transitions to the inferior surface (not labeled) via a tapered surface (not seen in the figures). The superior side of the second body portion 14 has a cylindrical protrusion/portion 36 that is sized to be pivotally/rotatably received in the arcuate portion 38. As such, the cylindrical protrusion 36 and the arcuate portion 38 defines a pivot/pivot point 37 such that the second body portion 14 pivots about the pivot 37 and relative to the first body portion 12 as is described in greater detail below. The second body portion 14 further defines opposite lateral sides or surfaces 24 and 26 that each extends between the superior and inferior sides thereof. The lateral sides 24, 26 are generally, but not necessarily flat.

The superior side 15 of the second body portion 14 has a gripping surface that is characterized by a plurality of serrations, teeth or teeth structures 46 that define plateaus and valleys for contact with an upper vertebral body (vertebra). The plurality of teeth 46 are configured to allow insertion of the second body portion 14 (and thus the fusion cage 10) via the anterior, posterior, or lateral side of the spine but prevent the backing out therefrom. In this regard, the teeth 46 are oriented accordingly (see e.g. FIGS. 1 and 3). Likewise, the inferior side of the second body portion 14 has a gripping surface that is characterized by a plurality of serrations, teeth or teeth structures 48 that define plateaus and valleys for contact with a lower vertebral body (vertebra). The plurality of teeth 48 are likewise configured to allow insertion of the second body portion 14 (and thus the fusion cage 10) via the anterior, posterior, or lateral side of the spine but prevent the backing out therefrom. In this regard, the teeth 48 are oriented accordingly.

The second body portion 14 moreover includes a second cavity 34 that extends between the superior side 15 and the inferior side (not labeled) of the second body portion 14. Bone fusion material is received in the second cavity 34 to promote vertebral fusion. As such, the second cavity 34 is open at the superior side and the inferior side of the second body portion 14.

Figure 2:
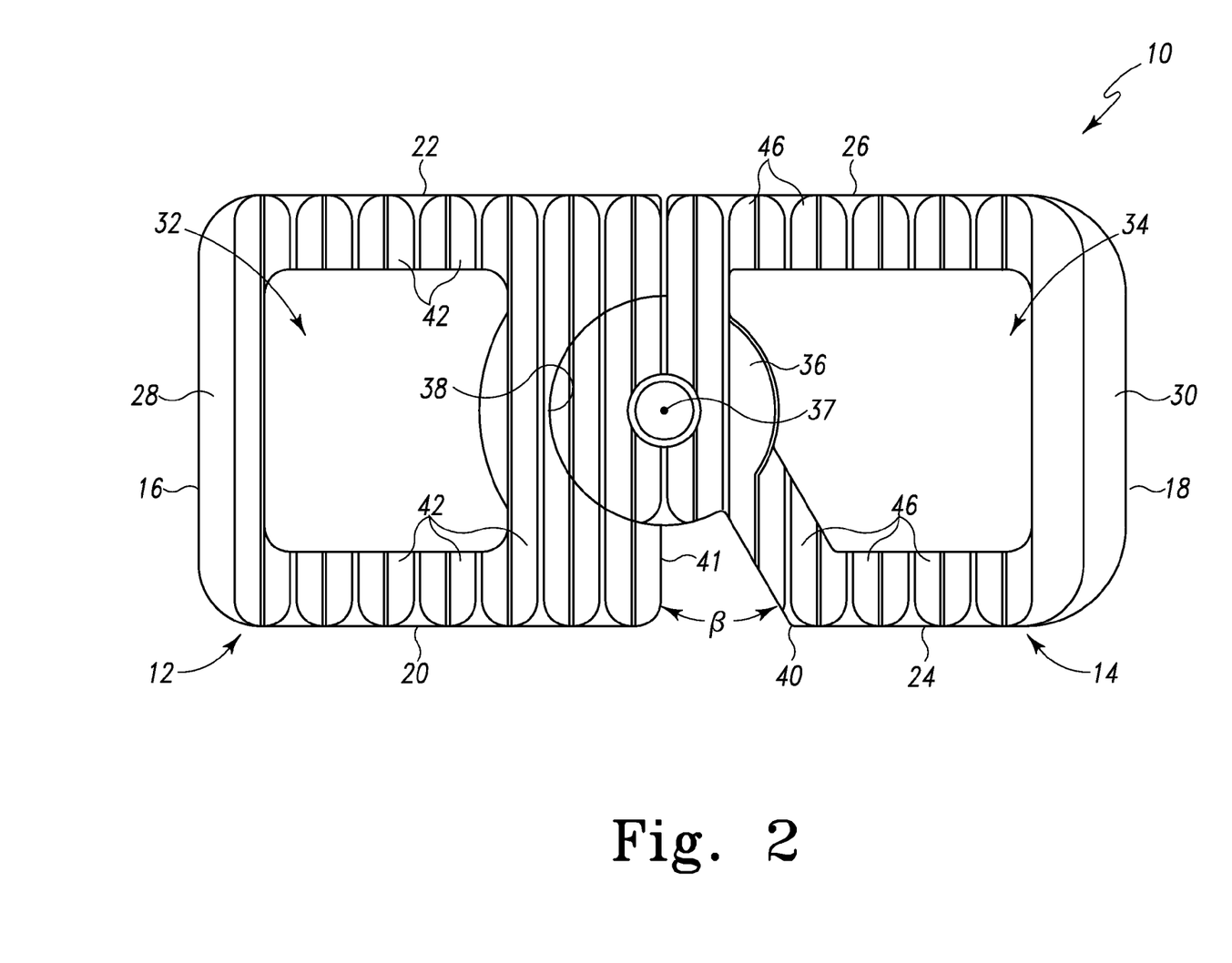
FIG. 2 is a superior plan view of the spinal interbody fusion cage of FIG. 1 with the pivoting portion thereof in the null or non-angled position.
Figure 4:
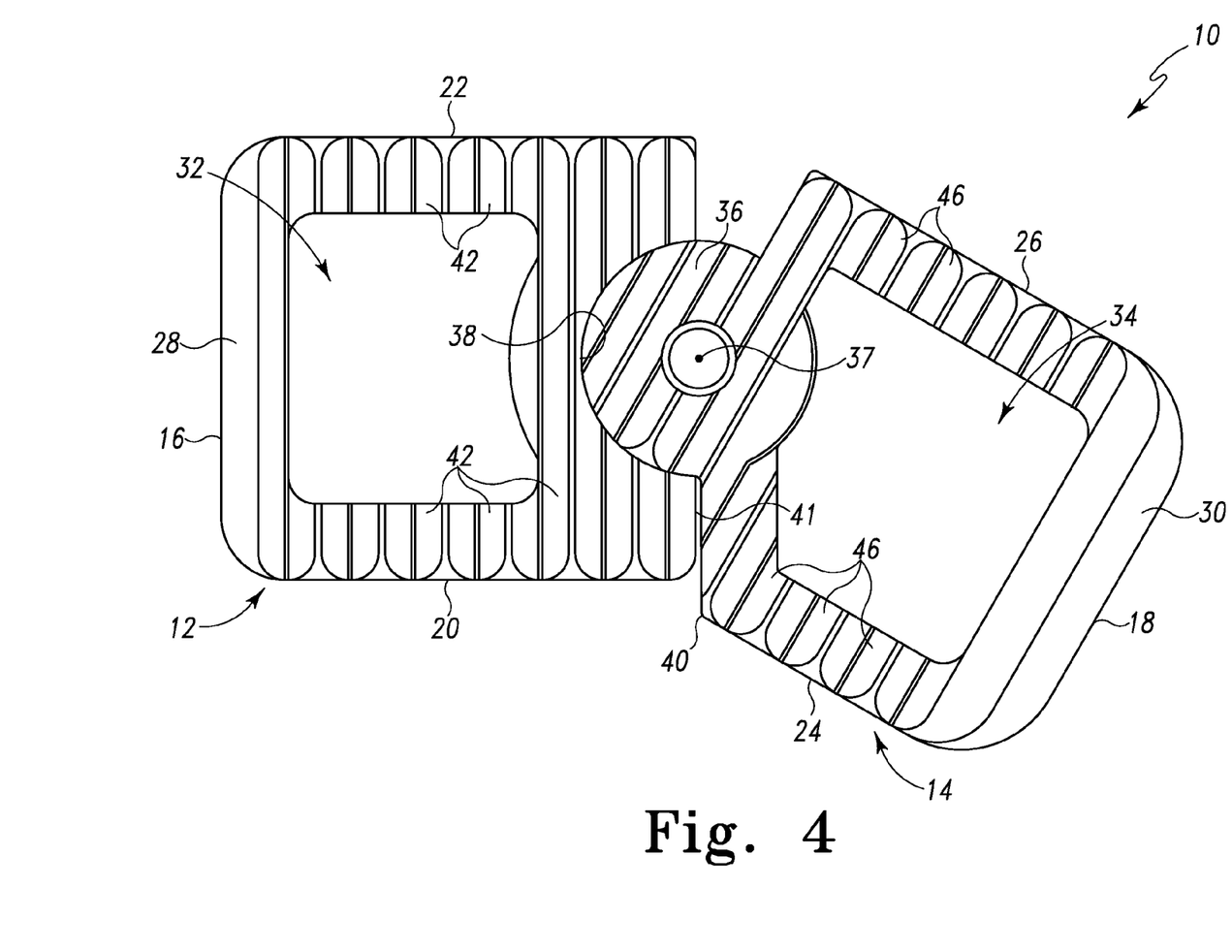
FIG. 4 is a superior plan view of the spinal interbody fusion cage of FIG. 1 with the pivoting portion thereof in the full angled position of FIG. 3.

As best seen in FIG. 2, the second body portion 14 has a posterior side wall or surface 40 that extends at an angle from the cylindrical protrusion 36 and is thus spaced from an anterior surface 41 of the first body portion 12. The space therebetween defines a distance or angle β. This distance or angle β allows the second body portion 14 to pivot relative to the first body portion 12 about the pivot 37 thus changing the anterior/posterior and lateral profile of the spinal interbody fusion cage 10. FIGS. 1 and 3 show the spinal interbody fusion cage 10 in a null or non-angle position while FIGS. 2 and 4 show the spinal interbody fusion cage 10 in a fully angled position. It should be appreciated that the second body portion 14 can be pivoted about the pivot 37 (and relative to the first body portion 12) such that the second body portion 14 can be positioned in any angular orientation from the null position to the fully angled position. The fully angled position is dependent on the angle or distance β between the wall 41 of the first body portion 12 and the angled wall 40 of the second body portion 14.

Figure 5A:
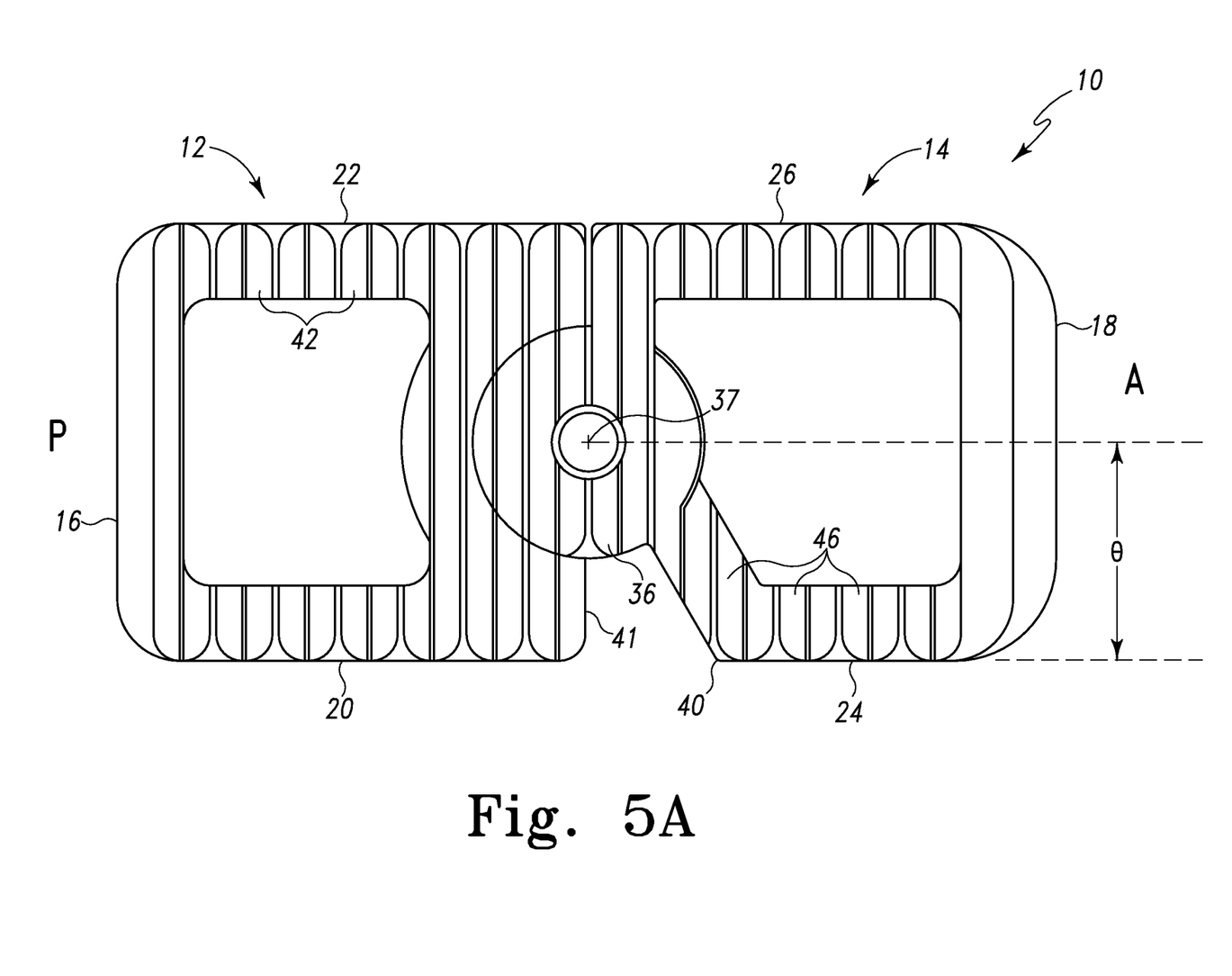
FIG. 5A depicts a superior plan view of the spinal interbody fusion cage of FIG. 1, which along with FIG. 5B, illustrates the range of lateral angulation of the pivoting portion or segment of the spinal interbody fusion cage body.
Figure 5B:
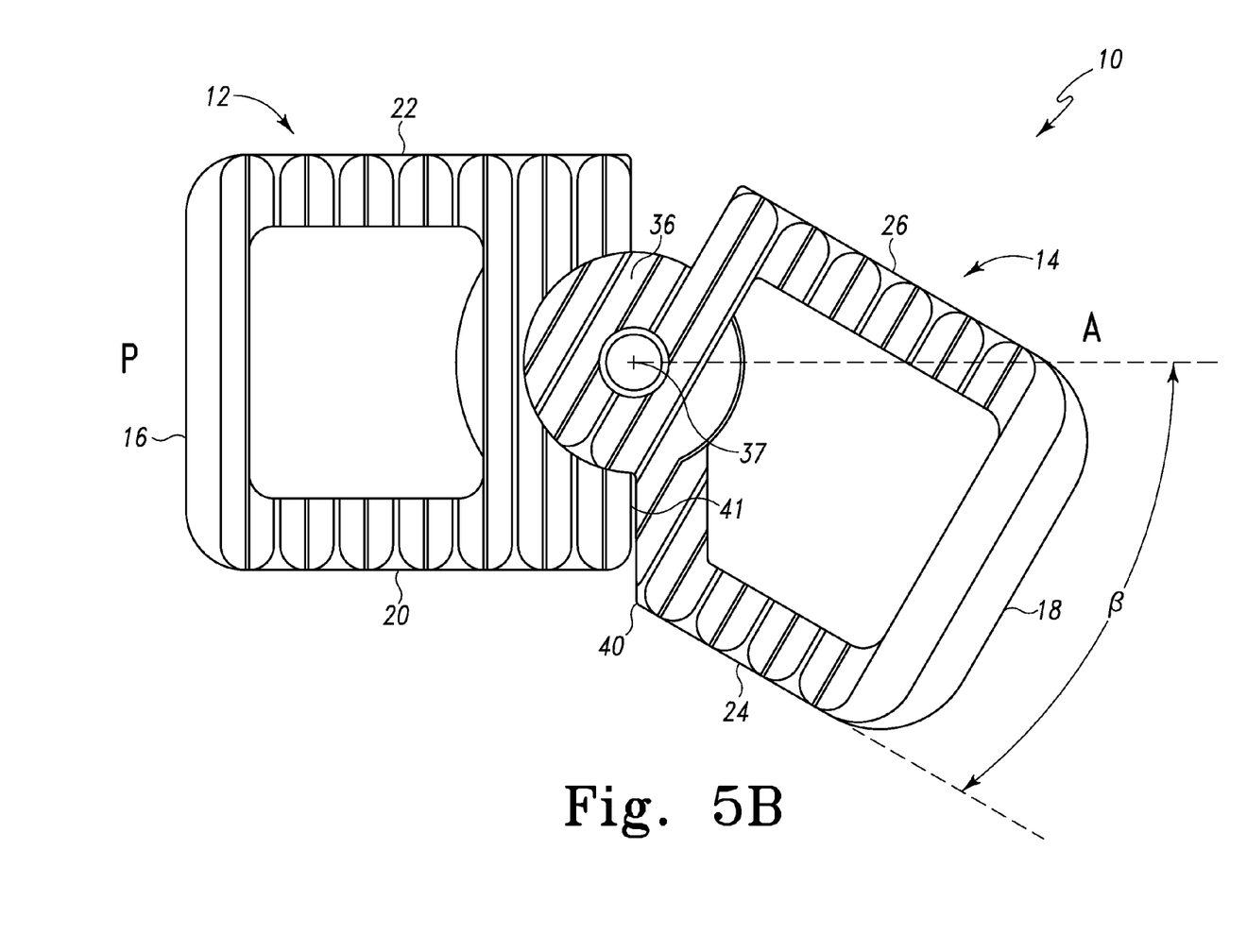
FIG. 5B depicts a superior plan view of the spinal interbody fusion cage of FIG. 1, which along with FIG. 5A, illustrates the range of lateral angulation of the pivoting portion or segment of the spinal interbody fusion cage body.

Referring to FIGS. 5A and 5B, there is depicted an illustration showing the null or non-angled position or profile of the spinal interbody fusion cage 10 (FIG. 5A) relative to the maximum or fully angled position or profile of the spinal interbody fusion cage 10 (FIG. 5B), relative to an axis therebetween. Again, it should be appreciated that the second body portion 14 may assume any position intermediate the null and fully angled positions (lateral angulation). The capital P stands for the posterior end of the fusion cage 10 while the capital A stands for the anterior end of the fusion cage 10. It can be seen that the angle or distance β between the wall 41 of the first body portion 14 and the angle wall 40 of the second body portion 14 translates into the angle β of travel of the second body portion 14 relative to the first body portion 12 (see FIG. 5B). In this manner, the anterior/posterior and thus the lateral profile of the spinal interbody fusion cage 10 may change as necessary while the superior/inferior height (double the height θ in FIG. 5A) remains constant.

Figure 6:
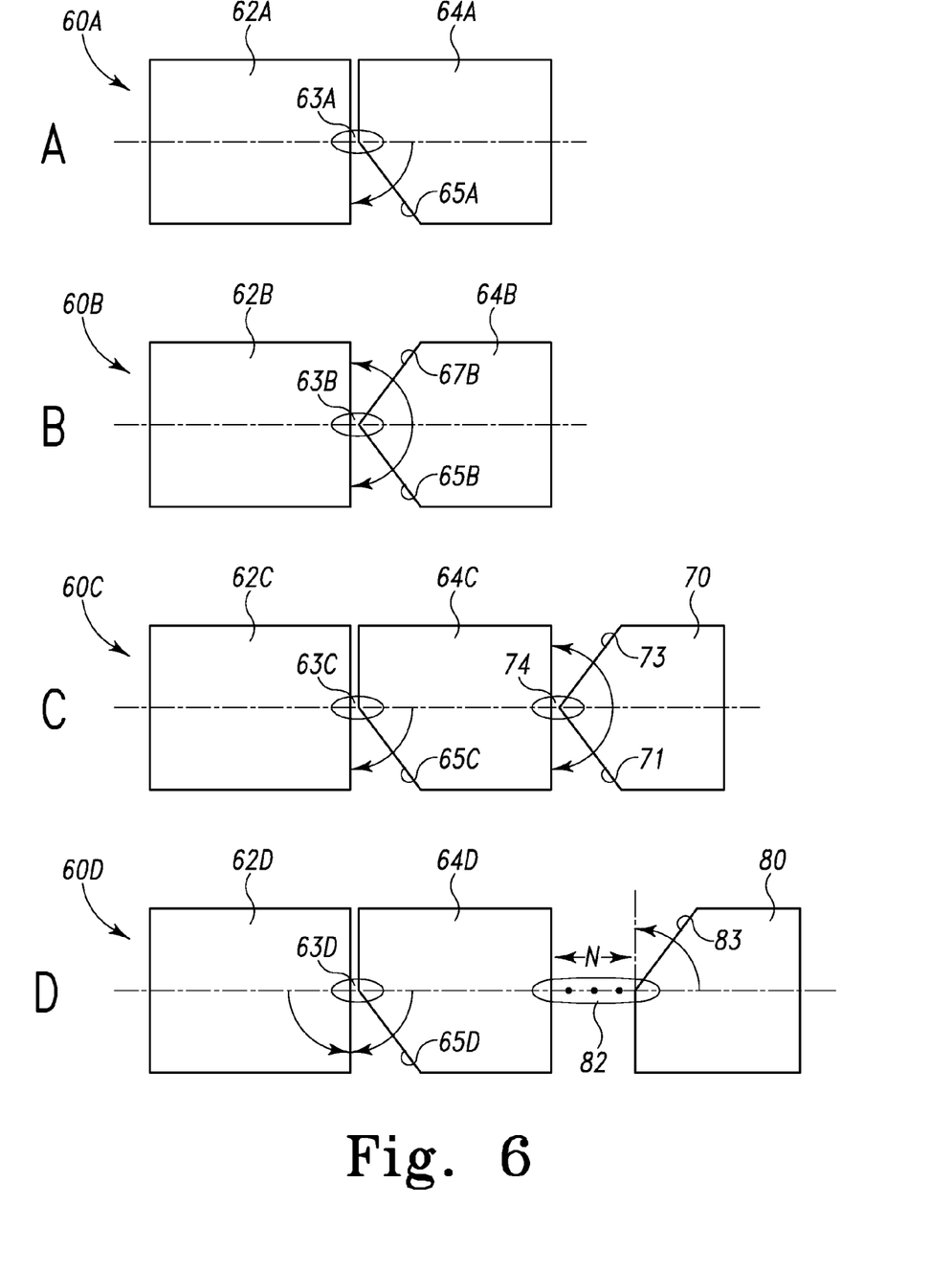
FIGS. 6A-D provide a diagrammatic illustration of various configurations of the present spinal interbody fusion cage achievable in accordance with the principles of the present invention.

FIGS. 1-5 illustrate a spinal interbody device whose lateral profile or curvature is changeable relative to the unchangeable superior to inferior height of the fusion cage, by utilizing articulation structures on the two segments, portions or sections of the body of the fusion cage. Surface configuration of the two segments provides for a given amount of articulation and thus curvature between the two segments. It should be appreciated, however, that the present invention is not limited to two segment (2-segment) embodiments. Referring to FIG. 6, there is provided an illustration of various N-segment spinal interbody fusion cages wherein the various segments have various configurations for variation in positioning. It should be appreciated that the various configurations shown in FIG. 6 are exemplary and thus for illustrative purposes only. Other configurations are known and contemplated, they being too numerous to show and describe herein.

In FIG. 6A, there is shown a 2-segment fusion cage 60A represented by segment 62A and segment 64A coupled to one another via articulation connection 63A. The segment 64A has an angled surface 65A that allows for articulation of the segment 64A relative to the segment 62A via the articulation connection 63A. The segment 64A may be moved into a variety of positions relative to segment 62A as represented by the arrow and ranging from a straight, null or posterior to anterior axis-aligned position (as shown) to a fully angled or curved position. This curvature is achievable in only one lateral direction relative to the posterior to anterior axis.

In FIG. 6B, there is shown another 2-segment fusion cage 60B represented by segment 62B and segment 64B coupled to one another via articulation connection 63B. The segment 64B has a first angled surface 65B that allows for articulation of the segment 64B relative to the segment 62B in a first (one) direction thereof via the articulation connection 63A. The segment 64B has a second angled surface 67B that allows for articulation of the segment 64B relative to the segment 62B in a second (another) direction thereof via the articulation connection 63A. The segment 64B thus has a range of directions of curvature and positions thereof as represented by the arrows. Particularly, the segment 64A may be moved into a variety of positions relative to segment 62A as represented by the arrows and ranging from a straight, null or posterior to anterior axis-aligned position (as shown) to a fully angled or curved position in both (side to side) lateral directions. Thus, curvature is achievable in both lateral directions relative to the posterior to anterior axis.

In FIG. 6C, there is shown a 3-segment fusion cage 60C represented by segment 62C, segment 64C and segment 70, with segments 62C and 64C coupled to one another via a first articulation connection 63C, and segments 64C and 70 coupled to one another via a second articulation connection 74. The segment 64C has an angled surface 65C that allows for articulation of the segment 64C relative to the segment 62C via the articulation connection 63C in one direction thereof. The segment 64C may be moved into a variety of positions, albeit in one direction, relative to segment 62C as represented by the arrow and ranging from a straight, null or posterior to anterior axis-aligned position (as shown) to a fully angled or curved position. Additionally, the segment 70 has a first angled surface 71 that allows for articulation of the segment 70 relative to the segment 64C in a first (one) direction thereof via the articulation connection 74. The segment 70 has a second angled surface 73 that allows for articulation of the segment 70 relative to the segment 64C in a second (another) direction thereof via the articulation connection 74. The segment 70B thus has a range of directions of curvature and positions thereof as represented by the arrows. Particularly, the segment 70 may be moved into a variety of positions relative to segment 64C independent of the positioning of the segment 64C relative to the segment 62C, as represented by the arrows and ranging from a straight, null or posterior to anterior axis-aligned position (as shown) to a fully angled or curved position in both (side to side) lateral directions. Thus, curvature is achievable in both lateral directions relative to the posterior to anterior axis. It should be appreciated that the third segment 70 may alternatively not be pivotally connected to the second segment 64C but may be fixed relative thereto.

FIG. 6D represents an N-segment spinal interbody fusion cage 60D. The N-segment fusion cage 60D is shown with first and second segments 62D and 64D coupled to one another via pivot 63D. Articulation therebetween is represented by the arrows and discernable via the geometry or configuration of the anterior and posterior surfaces of the segments 62D and 64D respectively. The N-segment fusion cage 60D is shown with N sections one or more of which are pivotally connected to one another, represented by connection 82. A last segment 80 is pivotally connected or not to the last of the N-segments. The last segment 80 may include geometry 83 for articulation as represented by the arrow.

Figure 7:
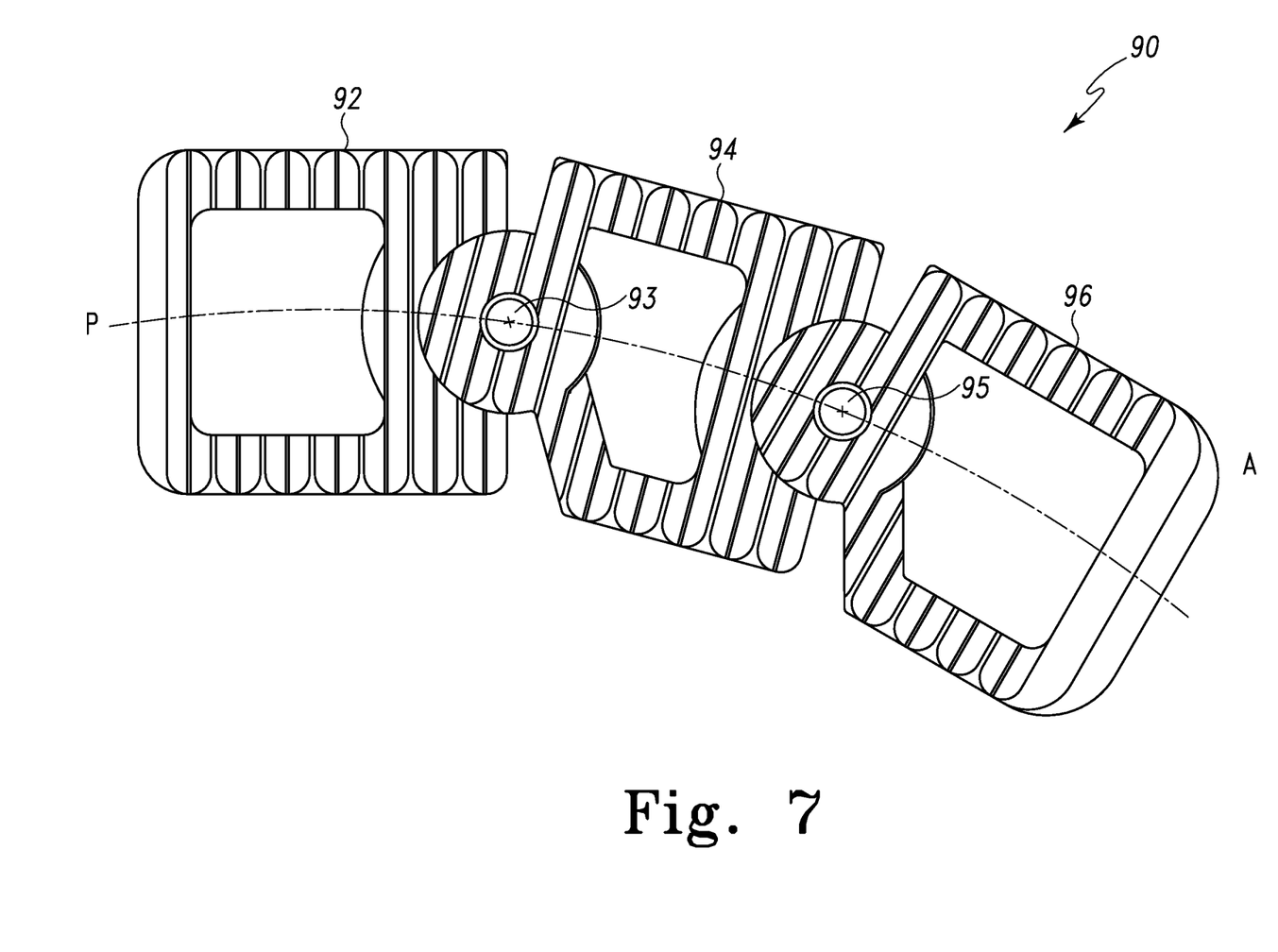
FIG. 7 is a top (superior) plan view of an N segment (shown as a 3-segment) embodiment of a spinal interbody fusion cage fashioned in accordance with the present principles, the 3-segment fusion cage articulated into an exemplary posterior to anterior curvature.

Referring to FIG. 7, there is depicted a three segment (3-segment) embodiment of an N-segment spinal interbody fusion cage generally designated 90. The N-segment spinal interbody fusion cage 90 is shown in a curved position from the posterior (P) to the anterior (A) thereof. In the 3-segment embodiment, a first segment 92 is pivotally connected to a second segment 94 via a first articulation joint 93, while a third segment 96 is pivotally connected to the second segment 94 via a second articulation joint 95. It can be easily seen that the first and second segments 92, 94 are movable relative to one another and independent of the movement between the second and third segments 94, 96.

While the invention has been illustrated and described in detail in the drawings and foregoing description, the same is to be considered as illustrative and not restrictive in character, it being understood that preferred embodiments have been shown and described and that all changes and modifications that come within the spirit of the invention are desired to be protected.

What is claimed is:

1. A spinal interbody fusion cage comprising:
a first segment having a first anterior sidewall and a second anterior sidewall; and
a second segment having a first posterior sidewall and a second posterior sidewall and pivotally connected to the first segment at a pivot point located at an intersection of the first and second anterior sidewalls of the first segment and at an intersection of the first and second posterior sidewalls of the second segment;
wherein the first posterior sidewall extends at an angle relative to the first anterior sidewall when the second posterior sidewall extends from the pivot point adjacent to the second anterior sidewall to define angular limits to the pivotal movement of the second segment;
wherein an anterior/posterior profile of the spinal interbody fusion cage is variable through angular positioning of the second segment relative to the first segment without changing a superior/inferior height of the spinal interbody fusion cage;
wherein the first and second anterior sidewalls extend between superior and inferior sides of the first segment and the first and second posterior sidewalls of the second segment extend between superior and inferior sides of the second segment, and wherein the superior and inferior sides of the first and second segments define the height of the spinal interbody fusion cage;
wherein the first segment comprises a first lateral sidewall and the second segment comprises a second lateral sidewall such that the first and second lateral sidewalls are substantially coplanar when the second posterior sidewall is adjacent and substantially parallel to the second anterior sidewall.

2. The spinal interbody fusion cage of claim 1, wherein the second segment is pivotally connected to the first segment via a pivot structure formed by and between the first and second segments.

3. The spinal interbody fusion cage of claim 2, wherein the pivot structure provides unidirectional pivotal movement between the first and second segments from a non-angled position.

4. The spinal interbody fusion cage of claim 2, wherein the pivot structure provides bi-directional pivotal movement between the first and second segments from a non-angled position.

5. The spinal interbody fusion cage of claim 2, wherein the pivot structure comprises a first pivot formation at an anterior end of the first segment and a second pivot formation at a posterior end of the second segment.

6. The spinal interbody fusion cage of claim 5, wherein the first pivot formation comprises an arced cavity, and the second pivot formation comprises an arced protrusion.

7. The spinal interbody fusion cage of claim 6, wherein the first segment has a first cavity therein, and the second segment has a second cavity therein.

8. The spinal interbody fusion cage of claim 7, wherein the first cavity extends from the superior side of the first segment to the inferior side of the first segment, and the second cavity extends from the superior side of the second segment to the inferior side of the second segment.

9. A spinal interbody fusion cage comprising:
a first segment having a first anterior sidewall and a second anterior sidewall; and
a second segment having a first posterior sidewall and a second posterior sidewall and coupled at an intersection of the first and second anterior sidewalls of the first segment and the first and second posterior sidewalls of the second segment for lateral articulation therewith;
wherein the first posterior sidewall extends from the intersection at an angle relative to the second posterior sidewall to define distance limits to the articulation;
wherein an anterior/posterior profile of the spinal interbody fusion cage is variable through lateral angular articulation of the second segment relative to the first segment without changing a superior/inferior height of the spinal interbody fusion cage;
wherein the first and second anterior sidewalls extend between superior and inferior sides of the first segment and the first and second posterior sidewalls extend between superior and inferior sides of the second segment, and wherein the superior and inferior sides of the first and second segments define the height of the spinal interbody fusion cage; and
wherein the first segment comprises a first lateral sidewall and the second segment comprises a second lateral sidewall such that the first and second lateral sidewalls are substantially coplanar when the second posterior sidewall is adjacent and substantially parallel to the second anterior sidewall.

10. The spinal interbody fusion cage of claim 9, wherein the first segment includes teeth disposed on the superior side thereof and on the inferior side thereof, and the second segment includes teeth disposed on the superior side thereof and on the inferior side thereof.

11. The spinal interbody fusion cage of claim 10, wherein the teeth on the superior side of the first segment extend from a posterior end of the first segment to an anterior end of the first segment, the teeth on the inferior side of the first segment extend from the posterior end of the first segment to the anterior end of the first segment, the teeth on the superior side of the second segment extend from a posterior end of the second segment to an anterior end of the second segment, and the teeth on the inferior side of the second segment extend from the posterior end of the second segment to the anterior end of the second segment.

12. The spinal interbody fusion cage of claim 9, wherein lateral articulation of the second segment relative to the first segment is provided by an articulation structure comprising a first articulation formation at an anterior end of the first segment and a second articulation formation at a posterior end of the second segment.

13. The spinal interbody fusion cage of claim 12, wherein the first articulation formation comprises an arced cavity, and the second articulation formation comprises an arced protrusion.

14. The spinal interbody fusion cage of claim 12, wherein the articulation structure provides lateral articulation of the second segment relative to the first segment at an angle from 0° to 90°.

15. The spinal interbody fusion cage of claim 14, wherein the first segment includes a first cavity therein, and the second segment has a second cavity therein.

16. The spinal interbody fusion cage of claim 15, wherein the first cavity is enclosed by lateral sidewalls that extend from the superior side of the first segment to the inferior side of the first segment, and the second cavity is enclosed by lateral sidewalls that extend from the superior side of the second segment to the inferior side of the second segment.

17. The spinal interbody fusion cage of claim 16, wherein the first and second segments are formed of one of PEEK, stainless steel or titanium.

18. A spinal interbody fusion cage comprising:
a first segment having a first anterior sidewall and a second anterior sidewall; and
a second segment having a first posterior sidewall and a second posterior sidewall and pivotally connected to the first segment at a pivot point located at an intersection of the first and second anterior sidewalls of the first segment and the first and second posterior sidewalls of the second segment;
wherein the first and second anterior sidewalls extend between superior and inferior sides of the first segment and the first and second posterior sidewalls extend between superior and inferior sides of the second segment, and wherein the superior and inferior sides of the first and second segments define a height of the spinal interbody fusion cage and are configured to facially engage vertebral bodies;
wherein the first segment and second segments each include a pair of lateral sidewalls, the pair of lateral sidewalls of the first segment being substantially coplanar with the pair of lateral sidewalls of the second segment when the second anterior sidewall is parallel to the second posterior sidewall.

19. The spinal interbody fusion cage of claim 18, wherein the first segment includes a first cavity therein extending entirely from a superior surface of the first segment to an inferior surface of the first segment, and the second segment has a second cavity therein extending entirely from a superior surface of the second segment to an inferior surface of the second segment.

20. The spinal interbody fusion cage of claim 19, wherein the first segment includes one or more sidewalls connecting the first anterior sidewall and the second anterior sidewall to define the first cavity, and the second cavity includes one or more sidewalls connecting the first anterior sidewall and the second anterior sidewall to define the second segment.

21. A spinal interbody fusion cage comprising:
a first segment having a first anterior sidewall and a second anterior sidewall; and
a second segment having a first posterior sidewall and a second posterior sidewall and pivotally connected to the first segment at a pivot point located at an intersection of the first and second anterior sidewalls of the first segment and at an intersection of the first and second posterior sidewalls of the second segment;
wherein the first posterior sidewall extends at an angle relative to the first anterior sidewall when the second posterior sidewall extends from the pivot point adjacent to the second posterior sidewall to define angular limits to the pivotal movement of the second segment;
wherein an anterior/posterior profile of the spinal interbody fusion cage is variable through angular positioning of the second segment relative to the first segment without changing a superior/inferior height of the spinal interbody fusion cage;
wherein the first segment has a first cavity therein, and the second segment has a second cavity therein, wherein the first cavity extends entirely from a superior surface of the first segment to an inferior surface of the first segment, and the second cavity extends entirely from a superior surface of the second segment to an inferior surface of the second segment, the first and second cavities configured to receive bone fusion material to promote fusion of adjacent vertebrae.

22. A spinal interbody fusion cage comprising:
a first segment having a first anterior sidewall and a second anterior sidewall; and
a second segment having a first posterior sidewall and a second posterior sidewall and pivotally connected to the first segment at a pivot point located at an intersection of the first and second anterior sidewalls of the first segment and at an intersection of the first and second posterior sidewalls of the second segment;
wherein the first posterior sidewall extends at an angle relative to the first anterior sidewall when the second posterior sidewall extends from the pivot point adjacent to the second posterior sidewall to define angular limits to the pivotal movement of the second segment;
wherein an anterior/posterior profile of the spinal interbody fusion cage is variable through angular positioning of the second segment relative to the first segment without changing a superior/inferior height of the spinal interbody fusion cage;
wherein the first segment includes teeth disposed on a superior side thereof and on an inferior side thereof, and the second segment includes teeth disposed on a superior side thereof and on an inferior side thereof;
wherein the teeth on the superior side of the first segment extend entirely from a posterior end of the first segment to an anterior end of the first segment, the teeth on the inferior side of the first segment extend entirely from the posterior end of the first segment to the anterior end of the first segment, the teeth on the superior side of the second segment extend entirely from a posterior end of the second segment to an anterior end of the second segment, and the teeth on the inferior side of the second segment extend entirely from the posterior end of the second segment to the anterior end of the second segment; and
wherein a lateral sidewall of the first segment is coplanar with a lateral sidewall of the second segment when the second anterior sidewall of the first segment is adjacent and parallel to the second posterior sidewall of the second segment; and wherein a first cavity passes entirely through the first segment in a superior/inferior direction and a second cavity passes entirely through the second segment in a superior/inferior direction, the first and second cavities configured to receive bone fusion material to promote fusion of adjacent vertebrae.

* * * * *